(12) United States Patent
Frederich et al.

(10) Patent No.: US 10,253,038 B2
(45) Date of Patent: Apr. 9, 2019

(54) FUSICOCCANE DERIVATIVES AND METHODS

(71) Applicant: Florida State University Research Foundation, Inc., Tallahassee, FL (US)

(72) Inventors: James H. Frederich, Tallahassee, FL (US); Anna E. Salvati, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/962,208

(22) Filed: Apr. 25, 2018

(65) Prior Publication Data

US 2018/0312518 A1 Nov. 1, 2018

Related U.S. Application Data

(60) Provisional application No. 62/492,632, filed on May 1, 2017.

(51) Int. Cl.
*C07D 493/08* (2006.01)
*C07D 493/18* (2006.01)

(52) U.S. Cl.
CPC ......... *C07D 493/08* (2013.01); *C07D 493/18* (2013.01)

(58) Field of Classification Search
CPC .......................... C07D 493/08; C07D 493/18
USPC ........................................................ 549/355
See application file for complete search history.

(56) References Cited

FOREIGN PATENT DOCUMENTS

WO WO-2017049352 A1 * 3/2017 ............ A01H 17/00

OTHER PUBLICATIONS

Automatic identification of terpenoid skeletons through 13C nuclear magnetic resonance data disfuntionalization by Marcelo Ferreira et al (Year: 2001).*
Dake et al., "A Synthetic Approach to the Fusicoccane A-B Ring Fragment Based on a Pauson—Khand Cycloadditoin/Norrish Type 1 Fragmentation," J. Org. Chem., 2008, 73:6711-6715.
Po et al., "Intramolecular [2+2]—Photocycloaddition/Thermal Fragmentation Approach toward 5-8-5 Ring Systems," Organic Letters, 2001, 3(18):2819-2821.
Randall et al., "[2+2] Photocycloaddition/Thermal Retrocycloaddition. A New Entry into Functionalized 5-8-5 Ring Systems," J. Am. Chem. Soc., 1999, 121:4534-4535.
Ruprah et al., "Studies Towards the Total Synthesis of Cycloaraneosene and Ophiobolin M: A General Strategy for the Construction of the 5-8 Bicycllic Ring System," Eur. J. Org. Chem., 2002, 3145-3152.

* cited by examiner

*Primary Examiner* — Rita J Desai
(74) *Attorney, Agent, or Firm* — Eversheds Sutherland (US) LLP

(57) ABSTRACT

Provided are fusicoccane derivatives and methods of making fusicoccane derivatives. The methods may include contacting a tethered chromophore with light to initiate a photoinduced pericyclic reaction cascade to form a 5-8-5 carbotricycle. The 5-8-5 carbotricycle may be further functionalized.

20 Claims, 3 Drawing Sheets

FUSICOCCANE DERIVATIVES AND METHODS

CROSS-REFERENCE TO RELATED APPLICATIONS

This application claims priority to U.S. Provisional Patent Application No. 62/492,632, filed May 1, 2017, which is incorporated herein by reference.

BACKGROUND 14-3-3 proteins regulate a diverse array of cellular client proteins by forming binary complexes (see, e.g., Fu, H. et al., *Ann. Rev. Pharmacol. Toxicol.* 2000, 40, 617-647). Some of these protein-protein interactions (PPIs) may play a direct role in the pathobiology of multiple types of cancer and neurological disorders, such as Alzheimer's disease and Parkinson's disease. 14-3-3 PPIs also may be involved in the pathobiology of diabetes and inflammation, and they may mediate the virulence of certain pathogenic bacteria and viruses. For at least these reasons, there is an interest in modulating 14-3-3 PPIs for therapeutic purposes.

Fusicoccin A and cotylenin A may offer an entry point to 14-3-3 PPI modulation. In plant biology, these phytotoxins are believed to target a preformed binary complex between 14-3-3 and plasma membrane $H^+$-ATPase (PMA2). Binding of fusicoccin A at the rim of this PPI interface may prolong the lifetime of the 14-3-3•PMA2 complex by 90-fold. This stabilizing effect may result in irreversible activation of PMA2, which, in turn, may stimulate rapid acidification of the cell wall.

Fusicoccin A and cotylenin A also may be active in human cell culture. Both molecules may sensitize cancer cells to apoptosis in combination with INF-α. The same regimen of fusicoccin A and cotylenin A and INF-α can be non-toxic to healthy cells. This targeted pro-apoptotic activity, while valuable, may reflect a complex pharmacology. Multiple cellular targets of fusicoccin A and cotylenin A have been identified, including a growing list of human 14-3-3 PPIs. This group includes estrogen receptor-α (ERα), which may be a master regulator of tumor proliferation expressed in the majority of breast cancers. Fusicoccin A has been identified as a possible stabilizer of a regulatory 14-3-3•ERα complex. Exposure of MCF-7 breast cancer cells to fusicoccin A (1.0 µM) may reduce or inhibit estradiol-stimulated ERα dimerization, downstream gene expression, and/or deceased cell proliferation. Thus, the anti-estrogenic activity of fusicoccin A may represent a new treatment approach for breast cancer types that are resistant to aromatase inhibitors and/or antiestrogen hormone therapy.

Although the non-optimized pharmacology of fusicoccin A and cotylenin A may directly impact cancer, the structural complexity of fusicoccin A, cotylenin A, and related fusicoccanes has left isolation from fungi as the only known way to access these molecules and their derivatives. The stabilizing properties of fusicoccin A and cotylenin A typically require the formation of multiple contact points with both proteins in 14-3-3•CP complexes.

Fusicoccadiene synthease has been identified, which is the terpene cyclase responsible for assembling the 5-8-5 carbotricycle of fusicoccin A from geranylgeranyl pyrophosphate. Dioxygenases that mediate key C—H oxidations in the biosynthesis of fusicoccin A also have been identified. These discoveries have seeded efforts to engineer biosynthetic entry to fusicoccanes.

By relying on strategy-level imitation of terpene biosynthesis, a fully synthetic route to di- and sesterterpenes harboring 5-8-5 carbotricycles has been developed. This approach may be valuable for preparing the ophiobolins from simple polyprenyl-derived starting materials. Access to the fusicoccane motif also has been reported; however, the direct application of this synthetic blueprint to the higher oxidation-state fusicoccin subfamily has not been demonstrated.

Other generalized approaches to 5-8-5 ring systems have been attempted. These include strategies that use UV-light to initiate cycloaddition reactions between tethered chromophores of notable complexity. It has been shown that diene tethers may provide entry to the 5-8-5 tricycle via metal-catalyzed [4+4] cycloaddition. The utility of a ring-expanding oxy-Cope strategy to prepare the fusicoccane nucleus also has been tested. These techniques, however, typically require lengthy sequences to assemble cyclization precursors, which impedes practical access to analogs and/or in-depth structural studies.

A complementary approach to fusicoccane variants has been developed that relies on semi-synthesis, wherein biosynthetic fusicoccin A and cotylenin A are prepared by fermentation, isolated, and then modified using chemical synthesis.

There remains a need for methods that overcome one or more of the foregoing disadvantages, including methods of synthesis that permit relatively easy access to the shared 5-8-5 core of fusicoccane derivatives. There also remains a need for fusicoccane derivatives, which may permit the selectivity for 14-3-3 PPI interfaces to be tailored.

BRIEF SUMMARY

Provided herein are methods that may address one or more of the foregoing limitations, such as by providing, at least in some embodiments, direct access to a 5-8-5 carbotricycle core, including the shared 5-8-5 core of fusicoccane derivatives. The fusicoccane derivatives that may be made by the methods provided herein include natural products and/or a range of non-natural derivatives.

In one aspect, methods are provided for forming a fusicoccane derivative. In embodiments, the methods include providing a tethered chromophore having a structure according to Formula (A)—

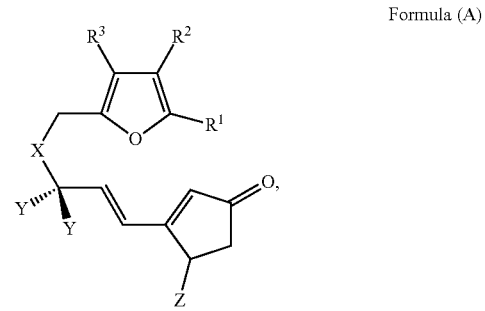

Formula (A)

wherein $R^1$, $R^2$, $R^3$, Y, and Z are independently selected from the group consisting of hydrogen, a monovalent $C_1$-$C_{20}$ hydrocarbyl, hydroxyl, and a protecting group, and X is —$CH_2$— or oxygen; and contacting the tethered chromophore with light comprising one or more wavelengths effective to initiate a photoinduced pericyclic reaction cascade to form a 5-8-5 carbotricycle.

In another aspect, methods of forming functionalized derivatives also are provided. In embodiments, the methods include providing a tethered chromophore having a structure according to Formula (A)—

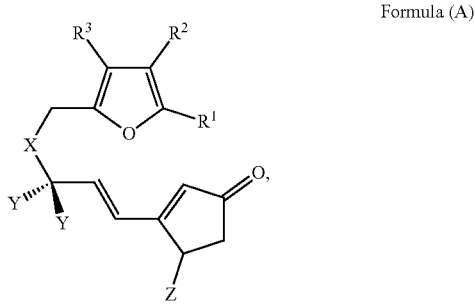

Formula (A)

wherein $R^1$, $R^2$, $R^3$, Y, and Z are independently selected from the group consisting of hydrogen, a monovalent $C_1$-$C_{20}$ hydrocarbyl, hydroxyl, and a protecting group, and X is —$CH_2$— or oxygen; and contacting the tethered chromophore with light comprising one or more wavelengths effective to initiate a photoinduced pericyclic reaction cascade to form a 5-8-5 carbotricycle; contacting the 5-8-5 carbotricycle with ($C_1$-$C_{20}$ hydrocarbyl)$_2$CuLi to form a conjugate alkylation product; contacting the alkylation product with a deprotonating agent and a leaving group precursor to form an enol product; and contacting the enol product with a ($C_1$-$C_{20}$ hydrocarbyl)Mg(halogen) to form a functionally active derivative, wherein the halogen is selected from Cl, Br, or I.

In yet another aspect, compounds are provided that have a structure according to Formula (B):

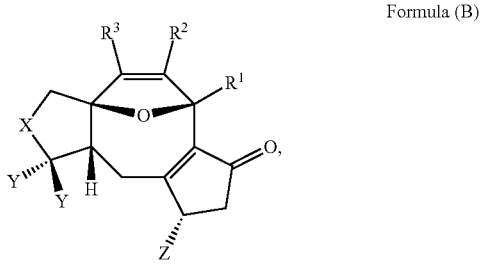

Formula (B)

wherein $R^1$, $R^2$, $R^3$, Y, and Z are independently selected from the group consisting of hydrogen, a monovalent $C_1$-$C_{20}$ hydrocarbyl, hydroxyl, and a protecting group; and X is —$CH_2$— or oxygen.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION

Figure 1:
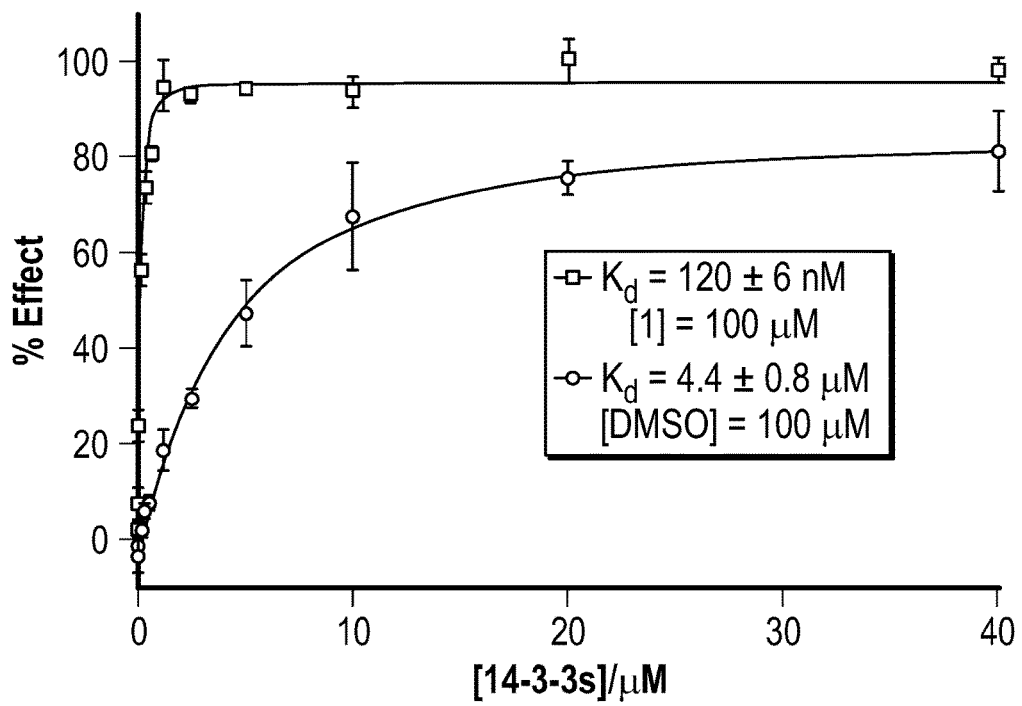
FIG. 1 depicts the results of an embodiment of a fluorescence polarization test.

In one aspect, methods of forming fusicoccane derivatives are provided. In embodiments, the methods include providing a tethered chromophore having a structure according to Formula (A)—

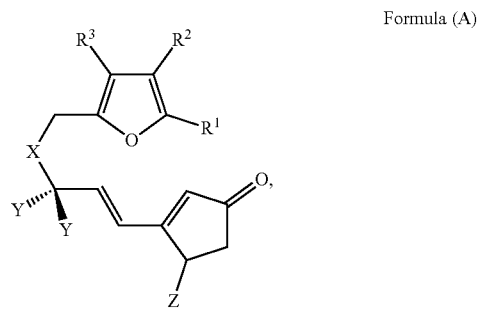

Formula (A)

wherein $R^1$, $R^2$, $R^3$, Y, and Z are independently selected from the group consisting of hydrogen, a monovalent $C_1$-$C_{20}$ hydrocarbyl, hydroxyl, and a protecting group, and X is —$CH_2$— or oxygen; and contacting the tethered chromophore with light comprising one or more wavelengths effective to initiate a photoinduced pericyclic reaction cascade to form a 5-8-5 carbotricycle.

As used herein, the phrase "5-8-5 carbotricycle" generally refers to a generic structure that includes an eight-member carbon atom ring to which two five-member carbon atom rings are fused. For example, an eight-member carbon atom ring may include [1] a first pair of bridgehead atoms that are members of the eight-member ring and members of a first five-member ring fused to the eight-member ring, and [2] a second pair of bridgehead atoms that are members of the eight-member ring and members of a second five-member ring fused to the eight-member ring. The first pair and second pair of bridgehead atoms may include any two adjacent carbon atoms of the eight-member ring. One or more of the carbon atoms of a 5-8-5 carbotricycle may be substituted as defined herein.

The light that is effective to initiate the photoinduced pericyclic reaction cascade may include a single wavelength or two or more wavelengths of light. When the light includes two or more wavelengths of light, the light may include at least one wavelength that is not effective to initiate a photoinduced pericyclic reaction cascade.

In some embodiments, a wavelength of light effective to initiate a photoinduced pericyclic reaction cascade is about 300 nm to about 400 nm, about 310 nm to about 390 nm, about 325 nm to about 375 nm, about 340 nm to about 360 nm. In another embodiment, a wavelength of light effective to initiate a photoinduced pericyclic reaction cascade is about 350 nm. The light generally may be provided by any known source. The contacting of the tethered chromophore with light may occur in any conditions (e.g., temperature, pressure, etc.) that permit a photoinduced pericyclic reaction cascade to occur at any rate.

The tethered chromophore having a structure according to Formula (A) may be made by any techniques known in the art. In some embodiments, the providing of the tethered chromophore of Formula (A) includes contacting a 5-halopent-1-yne with a furyl-metal reagent to form an alkyl furan; and contacting the alkyl furan with a cyclopentenone derivative to form the tethered chromophore.

The step of contacting the 5-halopent-1-yne with the furyl-metal reagent may occur at any conditions (e.g., temperature, pressure, etc.) that permit the alkyl furan to form. In some embodiments, the step of contacting the 5-halopent-1-yne with the furyl-metal reagent occurs at a temperature of about −10° C. to about 20° C., about −10° C. to about 10° C., or about −5° C. to about 5° C. In one embodiment, the step of contacting the 5-halopent-1-yne with the furyl-metal reagent occurs at a temperature of about 0° C.

The step of contacting the 5-halopent-1-yne with the furyl-metal reagent to form the alkyl furan may be conducted in the presence of any suitable solvent, such as tetrahydrofuran (THF).

Suitable solvents may include, but are not limited to, THF, N,N-dimethyl formamide (DMF), toluene, dichloromethane, hexamethylphosphoramide (HMPA), 1-methyl-2-pyrrolidinone (NMP), 1-ethyl-2-pyrrolidinone (NEP), 1,3-dimethyl-3,4,5,6-tetrahydro-2(1H)-pyrimidinone (DMPU), 1,3-dimethyl-2-imidazolindinone, or a combination thereof. One or more of the other processing elements described herein may be conducted in the presence of at least one of these solvents.

In some embodiments, the 5-halopent-1-yne may be contacted with at least 1.1 equivalents of the furyl-metal reagent. In one embodiment, the 5-halopent-1-yne is contacted with about 1.1 equivalents to about 3.0 equivalents, about 1.5 equivalents to about 2.5 equivalents, or about 2.0 equivalents of the furyl-metal reagent.

In some embodiments, the 5-halopent-1-yne has a structure according to the following formula:

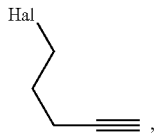

wherein Hal is Cl, Br, or I. In one embodiment, Hal is Cl. In another embodiment, Hal is Br. In yet another embodiment, Hal is I. The 5-halopent-1-yne may be substituted. For example, one or more of the sp3 hybridized carbon atoms of the 5-halopent-1-yne may be substituted as defined herein.

In some embodiments, the furyl-metal reagent includes a compound having a structure according to the following formula:

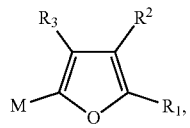

wherein $R^1$, $R^2$, and $R^3$ are independently selected from the group consisting of hydrogen, a monovalent $C_1$-$C_{20}$ hydrocarbyl, and a protecting group; and M is an alkali metal. In some embodiments, M is lithium. The $R^1$, $R^2$, and $R^3$ substituents may correspond to the $R^1$, $R^2$, and $R^3$ substituents of a tethered chromophore having a structure according to Formula (A). In some embodiments, $R^1$, $R^2$, and $R^3$ are hydrogen. In some embodiments, two of $R^1$, $R^2$, and $R^3$ are hydrogen, and one of $R^1$, $R^2$, and $R^3$ is a monovalent $C_1$-$C_{20}$ hydrocarbyl or a protecting group. In some embodiments, $R_1$ and $R_2$ are hydrogen, and $R_3$ is a methyl. In some embodiments, $R_1$ and $R_2$ are hydrogen, and $R_3$ is the protecting group. In some embodiments, $R_1$ and $R_2$ are hydrogen, and $R_3$ is [1] 1,3-dioxolan-2-yl, [2] a $C_1$-aldehyde, or [3] morpholin-4-yl. In some embodiments, $R_2$ and $R_3$ are hydrogen, and $R_1$ is [1] 1,3-dioxolan-2-yl, [2] a $C_1$-aldehyde, or [3]morpholin-4-yl. In some embodiments, $R_1$ is a methyl or a $C_1$-alcohol, and $R_2$ and $R_3$ are hydrogen. In some embodiments, two of $R^1$, $R^2$, and $R^3$ are hydrogen, and one of $R^1$, $R^2$, and $R^3$ is the monovalent $C_1$-$C_{20}$ hydrocarbyl or the protecting group.

In some embodiments, two of $R_{1-3}$ may be a $C_1$-$C_{20}$ hydrocarbyl, and the two $C_1$-$C_{20}$ hydrocarbyl moieties may be bonded to each other to form a cyclic structure.

The step of contacting an alkyl furan with a cyclopentenone derivative to form a tethered chromophore may occur in the presence of Schwartz's reagent. In one embodiment, the step of contacting an alkyl furan with a cyclopentenone derivative to form a tethered chromophore occurs in the presence of [1] Schwartz's reagent (($C_5H_5$)$_2$ZrHCl), Rh(cod)Cl$_2$ (Chloro(1,5-cyclooctadiene)rhodium(I) dimer), [2] (2,2'-bis(diphenylphosphino)-1,1'-binaphthyl) (BINAP), and [3] Mukaiyama's reagent (2-Chloro-1-methylpyridinium iodide). The contacting may occur at any conditions that permit the formation of a tethered chromophore. Each reagent may be introduced at the same temperature, or one or more of the reagents may be introduced at a different temperature.

In embodiments, the cyclopentenone derivative has a structure according to the following formula:

wherein Z is independently selected from the group consisting of hydrogen, a monovalent $C_1$-$C_{20}$ hydrocarbyl, hydroxyl, and a protecting group. The Z substituent may correspond with those of a tethered chromophore of Formula (A). In some embodiments, Z is hydrogen. In some embodiments, Z is a methyl. In some embodiments, Z is a protecting group. In some embodiments, Z is a hydrogen. The "Z" substituent may have any spatial orientation.

In some embodiments, the methods provided herein also include contacting a 5-8-5 carbotricycle with ($C_1$-$C_{20}$ hydrocarbyl)$_2$CuLi to form a conjugate alkylation product; contacting the alkylation product with a deprotonating agent and a leaving group precursor to form an enol product; and contacting the enol product with a ($C_1$-$C_{20}$ hydrocarbyl)Mg (halogen) to form a functionally active derivative, wherein halogen is selected from Cl, Br, or I.

The step of contacting the enol product with a ($C_1$-$C_{20}$ hydrocarbyl)Mg(halogen) to form a functionally active derivative may occur in the presence of a catalyst, such as PdCl$_2$-dppf (Bis(diphenylphosphino)ferrocene]dichloropalladium(II)). Any suitable catalysts may be used, however. Other suitable catalysts may include, but are not limited to, rhodium and palladium catalysts, including, but not limited to, Pd(0), Pd(II), and Rh(III) complexes, such as PdCl$_2$, Pd(OAc)$_2$, Pd(dba)$_2$, Pd2(dba)$_3$-CHCl$_3$, Rh(OAc)$_2$, or Rh(CO$_2$C$_{1-8}$ alkyl), wherein "dba" represents dibenzylideneacetone.

In embodiments, the (C$_1$-C$_{20}$ hydrocarbyl)$_2$CuLi is Me$_2$CuLi. In another embodiment, the deprotonating agent is potassium bis(trimethylsilyl)amide (KHMDS). In a further embodiment, the leaving group precursor is PhN(OTf)$_2$. In a particular embodiment, halogen is Br, and the (C$_1$-C$_{20}$ hydrocarbyl)Mg(halogen) is isopropenyl magnesium bromide.

In one embodiment, the (C$_1$-C$_{20}$ hydrocarbyl)$_2$CuLi is Me$_2$CuLi; the deprotonating agent is KHMDS; the leaving group precursor is PhN(OTf)$_2$; halogen is Br; and the (C$_1$-C$_{20}$ hydrocarbyl)Mg(halogen) is isopropenyl magnesium bromide.

In another aspect, compounds are provided herein, including compounds having a structure according to Formula (B):

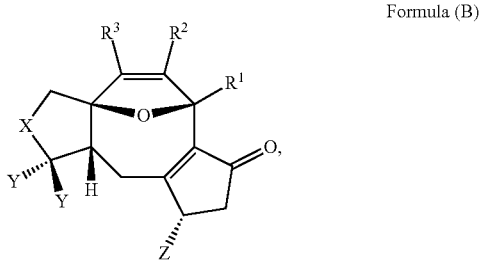

Formula (B)

wherein R$^1$, R$^2$, R$^3$, Y, and Z are independently selected from the group consisting of hydrogen, a monovalent C$_1$-C$_{20}$ hydrocarbyl, hydroxyl, and a protecting group; and X is —CH$_2$— or oxygen.

In some embodiments, R$^1$, R$^2$, and R$^3$ are hydrogen.

In some embodiments, two of R$^1$, R$^2$, and R$^3$ are hydrogen, and one of R$^1$, R$^2$, and R$^3$ is a monovalent C$_1$-C$_{20}$ hydrocarbyl or a protecting group.

In some embodiments, R$_1$ and R$_2$ are hydrogen, and R$_3$ is a methyl.

In some embodiments, R$_1$ and R$_2$ are hydrogen, and R$_3$ is the protecting group.

In some embodiments, R$_1$ and R$_2$ are hydrogen, and R$_3$ is [1] 1,3-dioxolan-2-yl, [2] a C$_1$-aldehyde, or [3] morpholin-4-yl.

In some embodiments, R$_2$ and R$_3$ are hydrogen, and R$_1$ is [1] 1,3-dioxolan-2-yl, [2] a C$_1$-aldehyde, or [3] morpholin-4-yl.

In some embodiments, R$_3$ is a methyl or a C$_1$-alcohol, and R$_1$ and R$_2$ are hydrogen. The C$_1$-alcohol may include a protected C$_1$-alcohol, such as —CH$_2$OTBS.

In some embodiments, two of R$_{1-3}$ may be a C$_1$-C$_{20}$ hydrocarbyl, and the two C$_1$-C$_{20}$ hydrocarbyl moieties may be bonded to each other to form a cyclic structure.

In some embodiments, Y and Z are hydrogen. In some embodiments, Y and Z are a methyl. In some embodiments, Y is hydrogen, and Z is a protecting group. In some embodiments, Z is hydrogen, and Y is a protecting group. In some embodiments, Y is hydrogen, and Z is a hydroxyl.

In embodiments, the compounds herein have a structure according to Formula (B), wherein R$^1$, R$^2$, and R$^3$ are hydrogen; and [a] Y and Z are hydrogen, [b] Y and Z are methyl, [c] Y is hydrogen and Z is a protecting group, [d] Y is a protecting group and Z is hydrogen, or [e] Y is a hydrogen and Z is a hydroxyl. In some embodiments, two of R$^1$, R$^2$, and R$^3$ are hydrogen; one of R$^1$, R$^2$, and R$^3$ is a monovalent C$_1$-C$_{20}$ hydrocarbyl or a protecting group; and [a] Y and Z are hydrogen, [b] Y and Z are methyl, [c] Y is hydrogen and Z is a protecting group, [d] Y is a protecting group and Z is hydrogen, or [e] Y is a hydrogen and Z is a hydroxyl. In some embodiments, R$_1$ and R$_2$ are hydrogen; R$_3$ is a methyl; and [a] Y and Z are hydrogen, [b] Y and Z are methyl, [c] Y is hydrogen and Z is a protecting group, [d] Y is a protecting group and Z is hydrogen, or [e] Y is hydrogen and Z is hydroxyl. In some embodiments, R$_1$ and R$_2$ are hydrogen; R$_3$ is the protecting group; and [a] Y and Z are hydrogen, [b] Y and Z are methyl, [c]Y is hydrogen and Z is a protecting group, [d] Y is a protecting group and Z is hydrogen, or [e]Y is hydrogen and Z is hydroxyl. In some embodiments, R$_2$ and R$_3$ are hydrogen; R$_1$ is [1] 1,3-dioxolan-2-yl, [2] a C$_1$-aldehyde, or [3] morpholin-4-yl; and [a] Y and Z are hydrogen, [b] Y and Z are methyl, [c] Y is hydrogen and Z is a protecting group, [d] Y is a protecting group and Z is hydrogen, or [e] Y is hydrogen and Z is hydroxyl. In some embodiments, R$_3$ is a methyl or a C$_1$-alcohol; R$_1$ and R$_2$ are hydrogen; and [a] Y and Z are hydrogen, [b] Y and Z are methyl, [c] Y is hydrogen and Z is a protecting group, [d] Y is a protecting group and Z is hydrogen, or [e] Y is a hydrogen and Z is a hydroxyl. In some embodiments, two of R$_{1-3}$ may be a C$_1$-C$_{20}$ hydrocarbyl, and the two C$_1$-C$_{20}$ hydrocarbyl moieties may be bonded to each other to form a cyclic structure.

In embodiments, the compounds provided herein have a structure according to one of Formulas B1-B9:

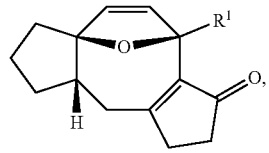

(Formula B1)

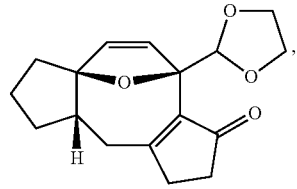

(Formula B2)

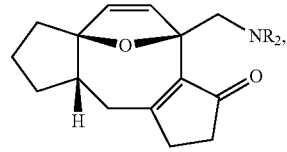

(Formula B3)

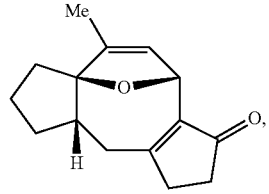

(Formula B4)

(Formula B5)
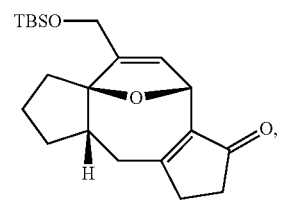

(Formula B6)
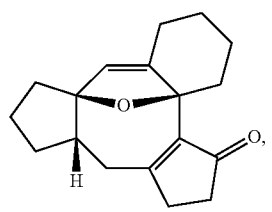

(Formula B7)
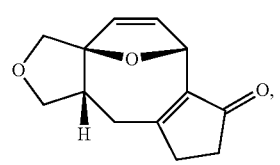

(Formula B8)
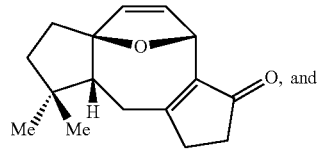

(Formula B9)
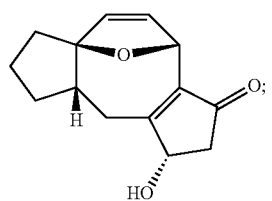

wherein $R^1$ is methyl or trimethylsilyl.

In some embodiments, the compound has a structure according to one of Formulas B10-B19:

Formula (B10)
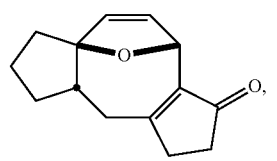

Formula (B11)
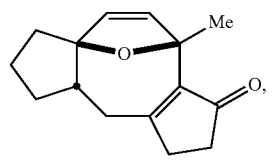

Formula (B12)
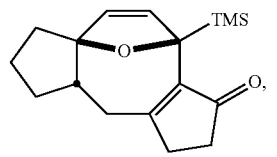

Formula (B13)
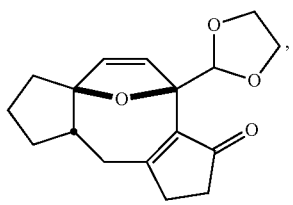

Formula (B14)
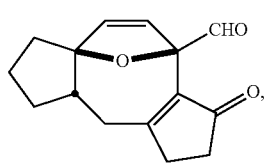

Formula (B15)
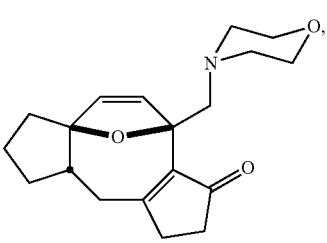

Formula (B16)
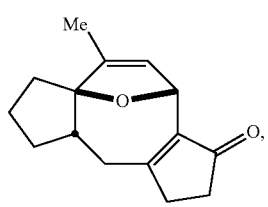

Formula (B17)
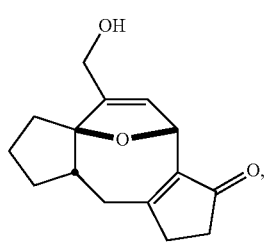

Formula (B18)
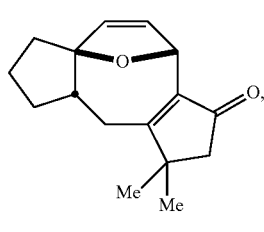

Formula (B19)
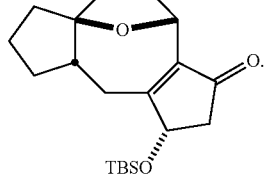

The phrase "$C_1$-$C_{20}$ hydrocarbyl," as used herein, generally refers to an aliphatic group, an aromatic or aryl group, a cyclic group, or any combination thereof; any substituted derivative thereof, including but not limited to any halide-, alkoxide-, or amide-substituted derivative thereof; or hydrogen. Also included in the definition of the $C_1$-$C_{20}$ hydrocarbyl are any unsubstituted, branched, or linear analogs thereof. The $C_1$-$C_{20}$ hydrocarbyl may be substituted with one or more functional moieties selected from a halide, an ether, a ketone, an ester, an amide, a nitrile, a heterocycle comprising at least one N-, O-, or S-heteroatom, an aldehyde, a thioether, an imine, a sulfone, a carbonate, a urethane, a urea, or an imide.

Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from 1 to 20 carbon atoms.

Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Examples of aryl or aromatic moieties include, but are not limited to, anthracenyl, azulenyl, biphenyl, fluorenyl, indan, indenyl, naphthyl, phenanthrenyl, phenyl, 1,2,3,4-tetrahydro-naphthalene, and the like, including substituted derivatives thereof, in each instance having from 6 to about 20 carbons. Substituted derivatives of aromatic compounds include, but are not limited to, tolyl, xylyl, mesityl, and the like, including any heteroatom substituted derivative thereof. Examples of cyclic groups, in each instance, include, but are not limited to, cycloparaffins, cycloolefins, cycloacetylenes, arenes such as phenyl, bicyclic groups and the like, including substituted derivatives thereof, in each instance having from about 3 to about 20 carbon atoms. Thus heteroatom-substituted cyclic groups such as furanyl are also included herein.

In each instance, aliphatic and cyclic groups are groups comprising an aliphatic portion and a cyclic portion, examples of which include, but are not limited to, groups such as: $(CH_2)_m C_6 H_q M_{5-q}$ wherein m is an integer from 1 to about 10, q is an integer from 1 to 5, inclusive; $(CH_2)_m C_6 H_q R_{10-q}$ wherein m is an integer from 1 to about 10, q is an integer from 1 to 10, inclusive; and $(CH_2)_m C_5 H_q R_{9-q}$ wherein m is an integer from 1 to about 10, q is an integer from 1 to 9, inclusive. In each instance and as defined above, M is independently selected from: an aliphatic group; an aromatic group; a cyclic group; any combination thereof; any substituted derivative thereof, including but not limited to any halide-, alkoxide-, or amide-substituted derivative thereof; any one of which has from 1 to about 20 carbon atoms; or hydrogen. In one aspect, aliphatic and cyclic groups include, but are not limited to: —$CH_2C_6H_5$; —$CH_2C_6H_4F$; —$CH_2C_6H_4Cl$; —$CH_2C_6H_4Br$; —$CH_2C_6H_4I$; —$CH_2C_6H_4OMe$; —$CH_2C_6H_4OEt$; —$CH_2C_6H_4NH_2$; —$CH_2C_6H_4NMe2$; —$CH_2C_6H_4NEt_2$; —$CH_2CH_2C_6H_5$; —$CH_2CH_2C_6H_4F$; —$CH_2CH_2C_6H_4Cl$; —$CH_2CH_2C_6H_4Br$; —$CH_2CH_2C_6H_4I$; —$CH_2CH_2C_6H_4OMe$; —$CH_2CH_2C_6H_4OEt$; —$CH_2CH_2C_6H_4NH_2$; —$CH_2CH_2C_6H_4NMe2$; —$CH_2CH_2C_6H_4NEt_2$; any regioisomer thereof, or any substituted derivative thereof. Thus, a cyclic group refers to groups such as $C_6H_qM_{5-q}$, $C_6H_qR_{10-q}$, $C_5H_qR_{9-q}$, and the like, where q, M, and R are defined immediately above.

In each instance, the heterocycle comprising at least one N-, O-, or S-heteroatom may be selected from the group consisting of: morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyi, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, or benzothiopyranyl S,S-dioxide.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O— alkyl- or —OC(O) NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

As used herein, the phrase "protecting group" refers to any moiety known in the chemical arts as capable of precluded undesired reactions at a protected site. Suitable protecting groups for the compounds described herein will be recognized from the present application taking into account the level of skill in the art, and with reference to standard textbooks, such as Greene, T. W. et al. Protective Groups in Organic Synthesis Wiley, New York (1991). Examples of suitable protecting groups include, but are not limited to, trifluoromethanesulfaonte (-OTf), t-butylmethylphenylsilyl, t-butyldiphenylsilyl, trimethylsilyl (TMS), triethylsilyl (TES), t-butyldimethylsilyl (TBS), o-nitrobenzyloxycarbonyl, p-nitrobenzyloxycarbonyl (pNZ), p-nitrobenzyl (pNB), benzyloxycarbonyl, t-butyloxycarbonyl, 2,2,2-trichloroethyloxycarbonyl and allyloxycarbonyl. Preferred protecting groups are TMS and TBS.

It must be noted that, as used in the specification and the appended claims, the singular forms "a," "an," and "the" include plural referents unless the context clearly dictates otherwise. Thus, for example, reference to "an aromatic compound" includes mixtures of aromatic compounds, and the like.

For any particular compound disclosed herein, any general structure presented also encompasses all conformational isomers, regioisomers, and stereoisomers that may arise from a particular set of substitutents. Thus, the general structure also encompasses all enantiomers, diastereomers, and other optical isomers whether in enantiomeric or racemic forms, as well as mixtures of stereoisomers, as the context requires.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified.

Moreover, all numerical end points of ranges disclosed herein are approximate. As a representative example, Applicant discloses, in one embodiment, that "a wavelength of light effective to initiate a photoinduced pericyclic reaction cascade is about 340 nm to about 360 nm". This range should be interpreted as encompassing values in a range of about 340 nm to about 360 nm, and further encompasses "about" each of 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, and 359 nm, including any ranges and sub-ranges between any of these values.

The processes described herein may be carried out or performed in any suitable order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Chemical Synthesis of Fusicoccane Derivatives

Scheme 1A depicts an embodiment of a modular, 2-step process to prepare tethered chromophores 5 from 5-iodopentyne, a furyl lithium reagent, and cyclopentenones.

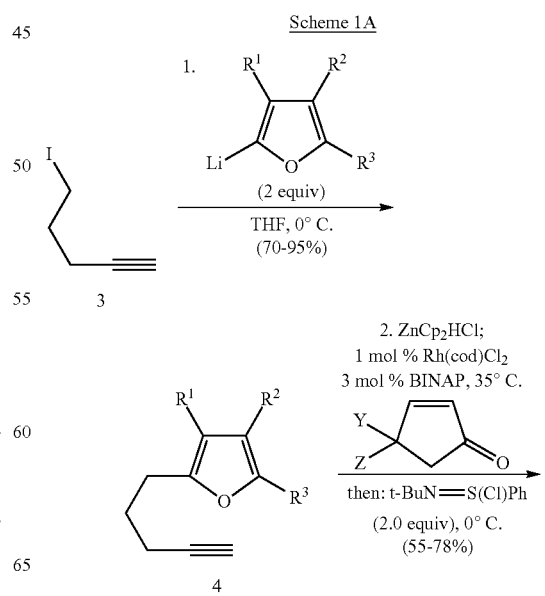

-continued

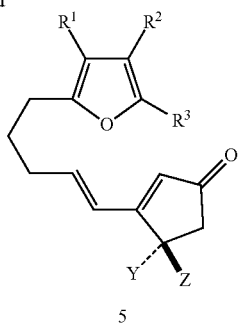

5

According to the embodiment depicted at Scheme 1A, 5-iodopentyne (3) was treated with 2 equivalents of furyl lithium in tetrahydrofuran (THF) at 0° C. to afford alkylfuran 4 at a yield of about 70% to about 95%.

This material was then reacted with Schwartz reagent to form a corresponding vinyl zirconium reagent, which was subsequently treated with a cyclopentenone derivative and a catalyst formed from $Rh(cod)C_{12}$ and 2,2'-bis(diphenylphosphino)-1,1'-binaphthyl (BINAP).

After 2 hours at 35° C., the corresponding zirconium enolate was intercepted in situ with Mukayiama's reagent to afford tether 5. This process also was scaled to provide about 15 g of tether 5 in a single pass.

Scheme 1B depicts an embodiment of a photoinduced pericyclic reaction cascade. The photoinduced pericyclic reaction cascade depicted at Scheme 1B directly converted tether 5 of Scheme 1A to 5-8-5 carbotricycle 8.

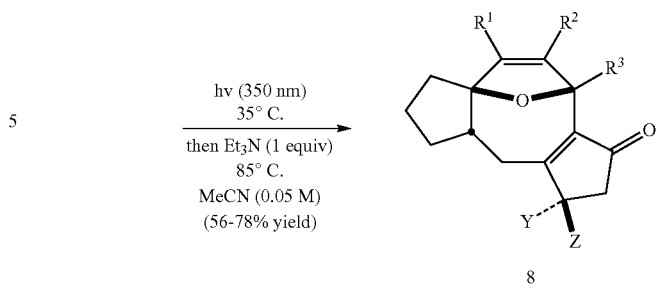

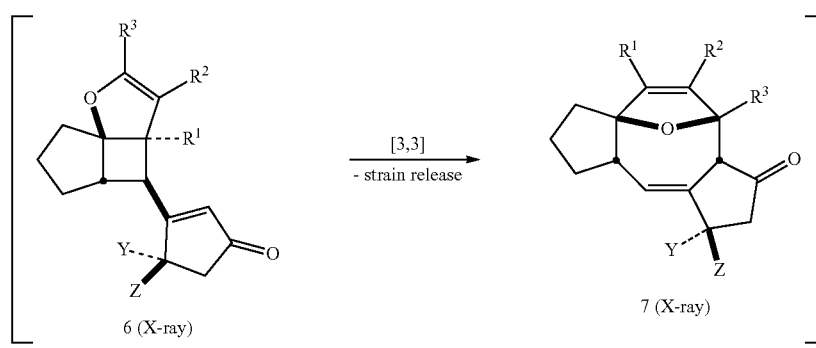

The mechanism of this process was studied. Exposure of tether 5 to UV-light (350 nm) at 35° C. was believed to initiate a [2+2] cycloaddition between the furan and dieneone to initially form cyclobutane 6. Warming the crude photolysate to 85° C. then appeared to trigger an internal Cope rearrangement, driven by strain release, to afford compound 7. Finally, an exogenous base isomerized compound 7 to enone 8. These results established that acyclic substrates like tether 5 could be used to prepare 5-8-5 carbocycles 8. The embodiments of this example furnished 8 as a single diastereomer.

The scope of the reaction cascade of this example was also explored. As shown at Table 1, this chemistry permitted the preparation of 5-8-5 carbotricycles including a range of different substitution patterns.

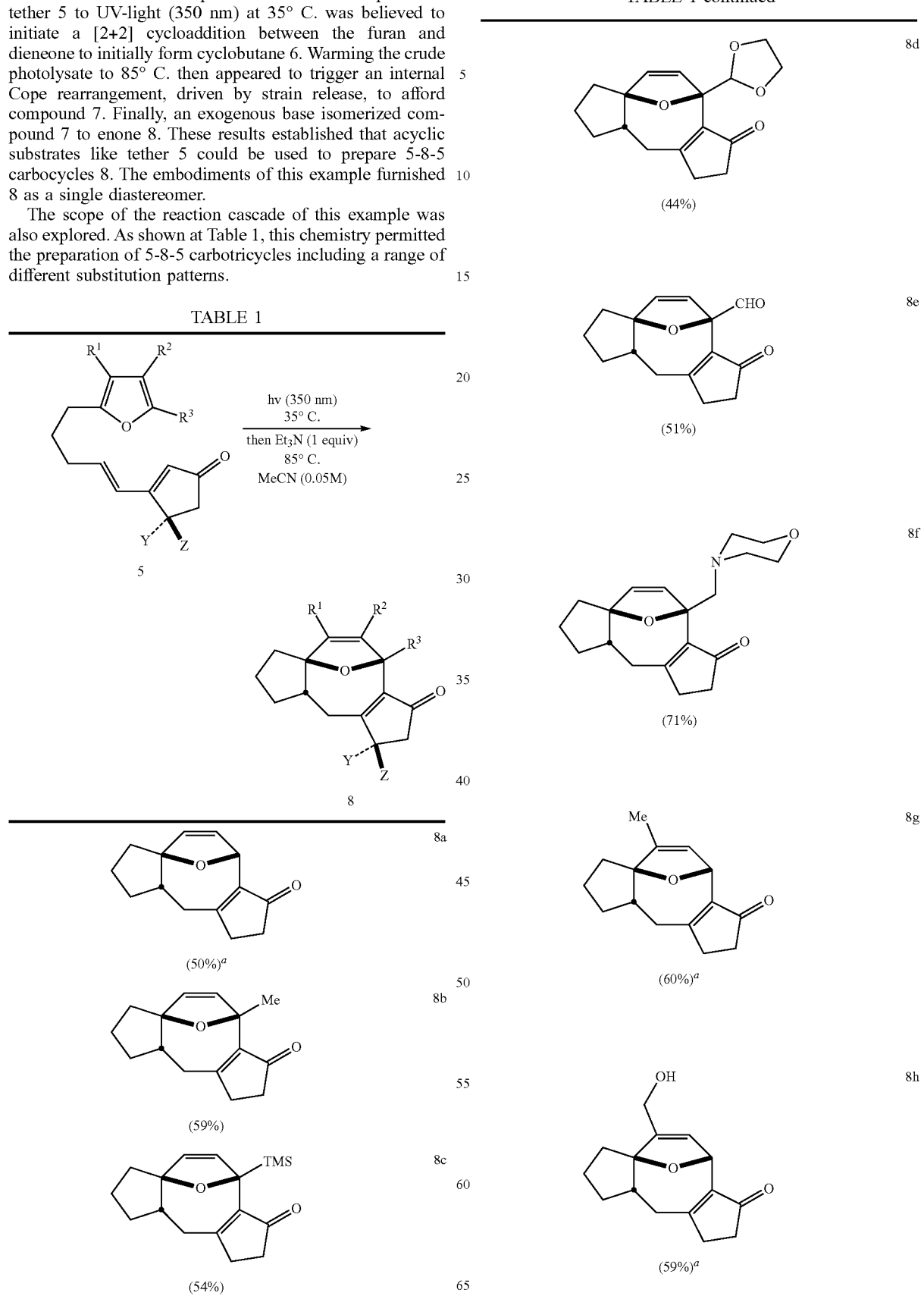

TABLE 1

TABLE 1-continued

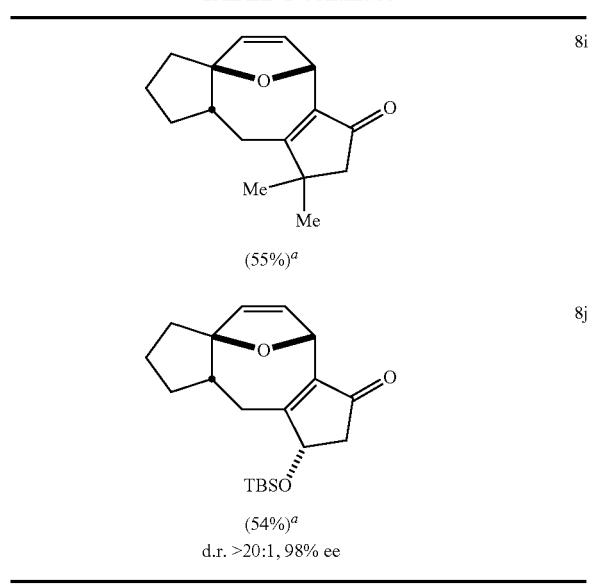

8i
(55%)[a]

8j
(54%)[a]
d.r. >20:1, 98% ee

[a]Reaction conditions: 0.05M n-BuOH, 35° C. then 100° C., no Et₃N.

The embodiments of this example offered flexibility to introduce functionality at one or more of positions $R^1$-$R^3$ of the furan ring (e.g., 8b-8h), and/or at least one of X and Y of the cyclopentenone group (e.g., 8i-8j).

In the embodiments of this example, the cascade reaction proceeded with control of relative stereochemistry. Substrate 8j was also prepared in high enantiomeric purity from enantioenriched tether 5j (Y=OTBS). These results indicated an efficient preparation of a fusicoccane nucleus.

Example 2—Synthesis of Functionally Active Derivatives

The synthetic compounds 8 of Example 1 were converted to functionally active derivatives. An embodiment of these conversion reactions is depicted at Scheme 2.

Scheme 2

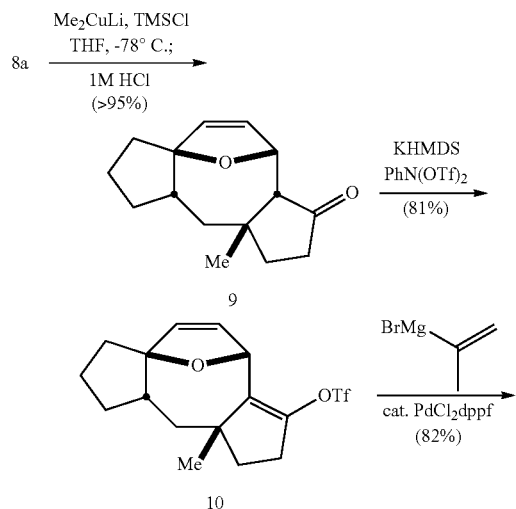

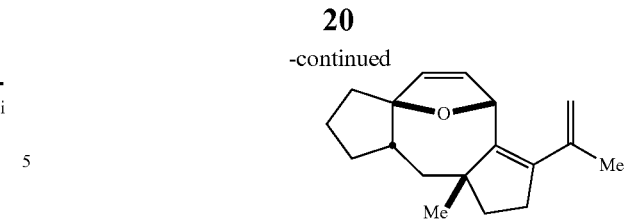

11

According to the embodiment of Scheme 2, the compound 8a was reacted with Me₂CuLi and trimethylsilylchloride (TMSCl) to furnish a conjugate alkylation product 9 as a single diastereomer after an aqueous workup.

Subsequent deprotonation under kinetic conditions and quenching with PhN(OTf)₂ afforded an enol triflate 10 in 81% yield. The enol triflate 10 was then cross-coupled with isopropenyl magnesium bromide utilizing PdCl₂dppf ([1,1'-bis(diphenylphosphino) ferrocene]dichloropalladium(II)) as a catalyst. This three-step protocol generated functional fusicoccane derivative 11 as a single diastereomer in excellent overall yield from the compound 8a. Other compounds, including compounds 8b-8j can be subjected to the foregoing process.

Example 3—Fusicoccane Derivatives that Stabilize 14-3-3 Protein-Protein Interactions The tests of this example demonstrate that embodiments of the synthetic intermediates described above function similarly to fusicoccin A (1) in vitro.

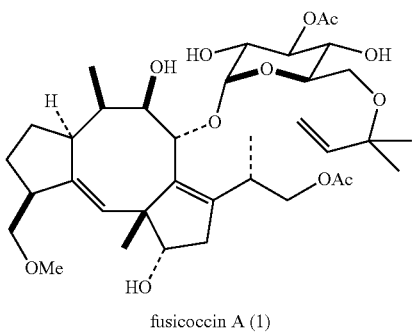

fusicoccin A (1)

Replicated in this example was Ottmann's characterization of interactions between 14-3-3σ and a synthetic hexapeptide of Task-3 containing the putative C-terminal 14-3-3-interaction motif KRRK-pS-V (Task-3 ctp). (Anders, C. et al., Chem. Biol. 2013, 13, 583-593).

Recombinant human 14-3-3σ was prepared using a bacterial expression protocol, which routinely produced 15 mg/L of purified protein. Recombinant 14-3-3σ was expressed in BL21 E. Coli cells and purified by Ni-affinity chromatography.

Utilizing isothermal titration calorimetry (ITC), it was found that Task-3 cpt binds to 14-3-3σ with a $K_d$ of 3.8±0.8 µM. This was determined by the association of ITC binding isotherms for Task-3 ctp with 14-3-3σ in the presence and absence of 100 µM of fusicoccin A (1). In the presence of fusicoccin A (1) (100 µM) the $K_d$ value decreased to 25±3 nM, revealing a 152-fold stabilization.

The titration protocol was adapted to 96-well plate format using fluorescence polarization (FP) experiments. FP measurements of fluorescein-labeled Task-3 ctp, in the absence and presence of 100 μM fusicoccin A (1), titrated with 14-3-3σ were used to obtain the apparent $K_d$ of the 14-3-3σ•Task-3 ctp interaction. Employing the fluorescein-labeled version of Task-3 ctp, it was found that the apparent affinity of Task-3 ctp to 14-3-3σ was enhanced by 37-fold, from a $K_d$ of 4.4±0.8 μM to a $K_d$ of 120±6 nM, when titrated in the presence of 100 μM fusicoccin A (1), as depicted at FIG. 1. Also collected were FP measurements of fluorescein-labeled c-Raf peptide, in the absence and presence of 100 μM fusicoccin A (1), titrated with 14-3-3σ to obtain the apparent $K_d$ of the 14-3-3σ•c-Raf peptide interaction. In the absence of fusicoccin A (1), a $K_d$ of 29±4.4 μM was observed, and, in the presence of fusicoccin A (1), a $K_d$ of 27±1.1 μM was observed.

Figure 2:
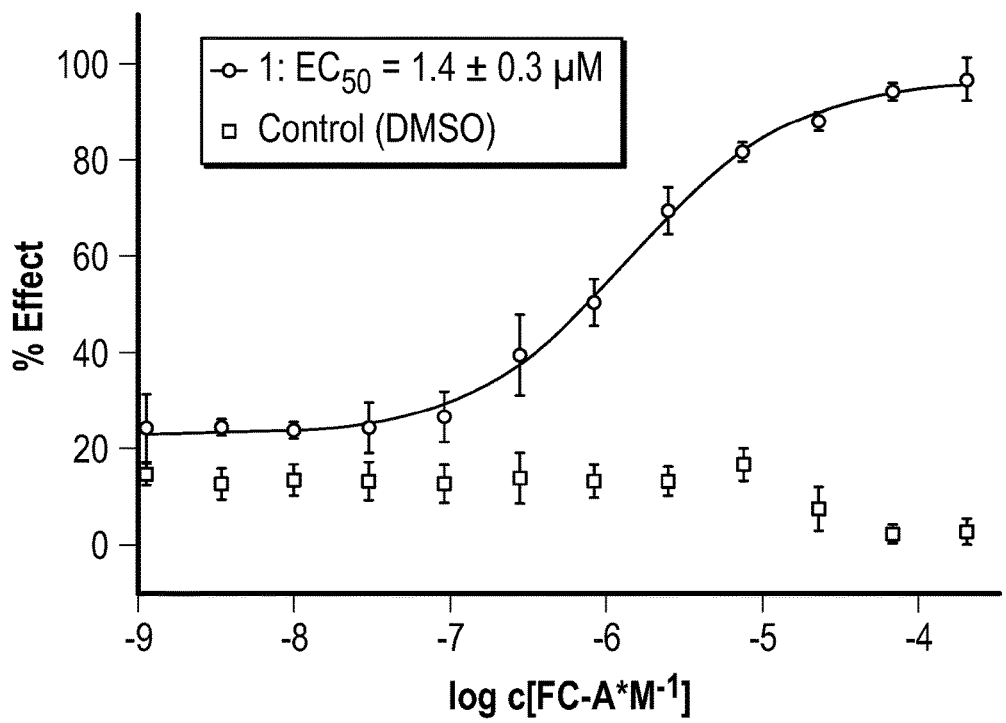
FIG. 2 depicts the results of an embodiment of a fluorescence polarization test.

It also was determined that fusicoccin A (1) stabilized the 14-3-3σ•Task-3 ctp complex with an $EC_{50}$ of 1.4±0.3 μM, as depicted at FIG. 2. FP measurements of fluorescein-labeled Task-3 ctp and 14-3-3σ titrated with fusicoccin A (1) were used to obtain $EC_{50}$ values (FIG. 2) for its stabilizing activity toward the 14-3-3σ•Task-3 ctp interaction. Error bars indicate the mean±SD of three independent experiments.

Figure 3:
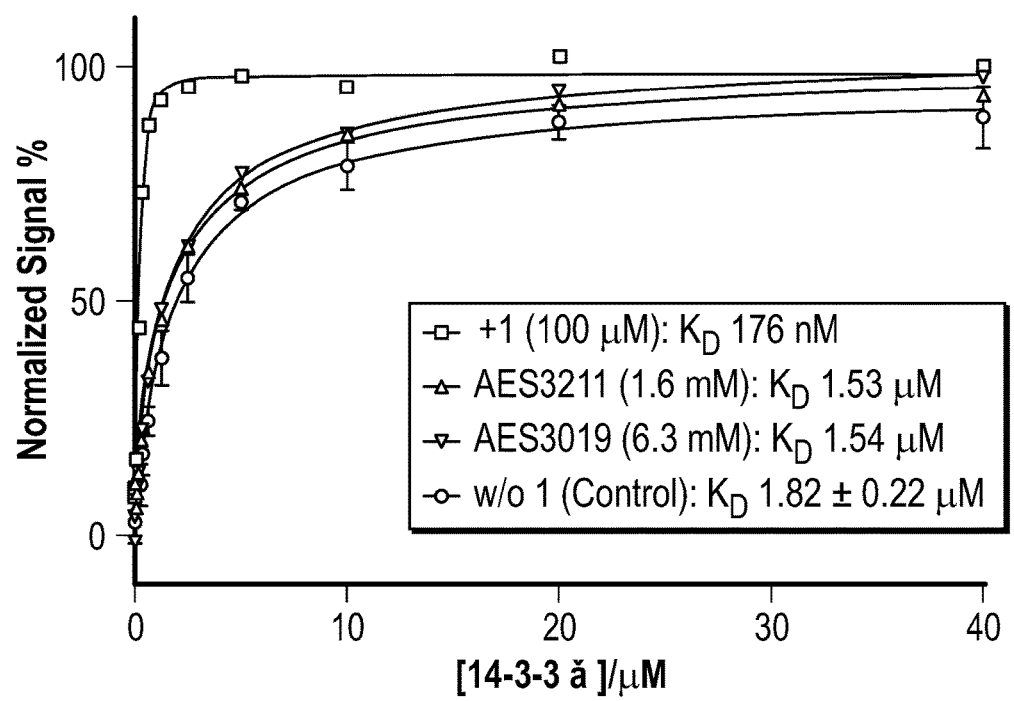
FIG. 3 depicts data collected from embodiments of structures that stabilize 14-3-3σ•Task-3 ctp PPI in vitro.

In view of the foregoing control data, a library of synthetic derivatives, including 8a-j, 9-11, was screened for functional interactions 14-3-3σ•Task-3 ctp complex. The results revealed that structures 8f and 11 increase the apparent affinity of Task-3 ctp for 14-3-3σ in vitro (FIG. 3). Compounds 8f and 11 have the following structures:

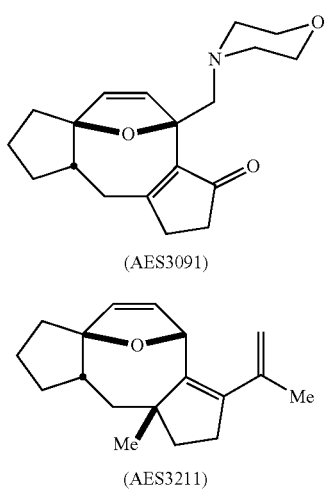

(AES3091) 8f (AES3211) 11

Using DMSO (10%) as a part of the buffer composition, it was found that the apparent affinity of Task-3 ctp to 14-3-3σ was enhanced by 1.2-fold, from a $K_d$ of 1.82±0.22 μM to a $K_d$ of 1.54 μM, when titrated in the presence of 1.6 mM of compound 11.

Similarly, the apparent affinity of Task-3 ctp to 14-3-3σ was enhanced by 1.1-fold, from a $K_d$ of 1.82±0.22 μM to a $K_d$ of 1.55 μM, when titrated in the presence of 6.3 mM of compound 8f.

Other screened compounds were statistically identical to the control curve in the absence of fusicoccin A (1). Although derivatives 8f and 11 only induced a small increase in the lifetime of the 14-3-3σ•Task-3 ctp complex, they nonetheless constituted fully synthetic stabilizers of the 14-3-3 PPI. The identification of functional analogs 11 and 8f provided proof-of-concept that the chemotypes herein, include those prepared via the methods herein, can have direct application as PPI modulators.

Example 4—Experimental Details

The compound (E)-2-(5-iodopent-4-en-1-yl)furan (4a) was made according to the following procedure. A solution of n-BuLi (1.95 M in THF, 133 mL, 260 mmol) was added drop-wise via addition funnel to a solution of furan (28.4 mL, 390 mmol) in THF (200 mL) at 0° C. The reaction was maintained at 0° C. for 4 hours, then 5-iodopentyne (19.4 g, 100 mmol) was added to the mixture via syringe. The resulting solution was allowed to slowly warm to ambient temperature. After 8 hours, the reaction mixture was treated with saturated aqueous $NH_4Cl$ (100 mL). The resulting slurry was added to a separation funnel and the organic layer was isolated. The aqueous layer was washed with $Et_2O$ (3×100 mL). The combined organics were dried over $MgSO_4$, filtered, and concentrated under reduced pressure. The resulting crude oil was purified by distillation to afford compound 4a (11.5 g, 85.9 mmol, 86%) as a colorless oil. Characterization data was substantially identical to previously reported values (see, e.g., Yamamoto, H. et al., Org. Lett. 2007, 9, 1399-1402).

The compound (E)-3-(5-(furan-2-yl)pent-1-en-1-yl)cyclopent-2-en-1-one (5a) was made according to the following procedure. A suspension of $ZrCp_2HCl$ (1.70 g, 6.60 mmol) in THF (20 mL) was treated with compound 4a (0.811 g, 6.00 mmol) at room temperature. In a separate flask, a suspension of $Rh[cod]Cl_2$ (31 mg, 0.062 mmol, 1.2 mol %), BINAP (94 mg, 0.15 mmol, 3 mol %), and 2-cyclopenten-1-one (0.4 mL, 5 mmol) in THF (5 mL) was maintained at room temperature. After 1 hour, the vinyl zirconium reagent generated from compound 4a was added to the catalyst mixture via syringe. The resulting dark solution was warmed to 30° C. After 3 hours, the reaction mixture was cooled to room temperature and treated with a 1.0 M solution of N-tert-butylbenzenesulfinimidoyl chloride (11.3 mL, 11.25 mmol) in benzene. The resulting mixture reaction was allowed to warm to room temperature over 2 hours and maintained at room temperature for 1 hour. The reaction was then quenched with saturated $NaHCO_3$ (10 mL), diluted with EtOAc (60 mL), and rapidly stirred for 15 minutes. The resulting slurry was extracted with EtOAc (3×20 mL). The combined organic extracts were washed with brine (20 mL), dried over $MgSO_4$, filtered, and concentrated. The resulting crude residue was purified by flash column ($SiO_2$, 97:3 $CH_2Cl_2/Et_2O$) to afford compound 5a (0.821 g, 3.80 mmol, 76%) as a yellow oil: (1.30 g, 6.00 mmol, 60%) as yellow oil: $^1H$ NMR (400 MHz, $CDCl_3$) δ 7.31 (t, J=0.9, 1H), 6.55 (d, J=15.8, 1H), 6.30 (dt, J=7.2, 7.0, 1H), 6.28-6.27 (m, 1H), 6.00 (d, J=3.1, 1H), 5.96 (br s, 1H), 2.72 (m, 2H), 2.67 (t, J=7.4, 2H), 2.45 (m, 2H), 2.28 (q, J=7.2, 2H), 1.83 (pent, J=7.5, 2H) $^{13}C$ NMR (100 MHz, $CDCl_3$) δ C: 209.6, 172.6, 155.4; CH: 140.9, 140.1, 129.3, 127.1, 110.1, 105.2; $CH_2$: 34.8, 32.5, 27.4, 27.1, 27.0; HRMS-ESI (m/z) [M]+ calculated for $C_{14}H_{16}O_2Na$=239.1048; found 239.1054.

The compound (±)-1,2,3,6,8,9,10,10a-octahydro-7H-3a, 6-epoxydicyclopenta[a,d][8]annulen-7-one (8a) was made according to the following procedure. A solution of (E)-3-(5-(furan-2-yl)pent-1-en-1-yl)cyclopent-2-en-1-one (1.00 g, 4.64 mmol) in freshly distilled 1-butanol (77 mL) was irradiated in a Rayonet photoreactor at 350 nm for 34.5 hours. The reaction mixture was then removed from the photoreactor and heated at 100° C. for 1 hour. The solution was cooled to room temperature and concentrated to afford a yellow oil. The crude oil was purified by flash chromatography (pH 7 buffered $SiO_2$, 2:1 hexanes/EtOAc) to afford compound 8a (0.527 g, 2.44 mmol, 53%) as yellow solid: mp=50.8-51.3° C.; $^1$H NMR (400 MHz, $CDCl_3$) δ 6.08 (d, J=5.9, 1H), 5.86 (dd, J=5.9, 1.8, 1H), 5.45 (br. s, 1H), 2.55-2.46 (m, 3H), 2.41-2.25 (m, 2H), 2.16-2.11 (m, 2H), 1.93-1.70 (m, 5H), 1.32-1.25 (m, 1H); $^{13}$C NMR (150 MHz, $CDCl_3$) δ C: 206.7, 176.3, 142.1, 96.6; CH: 129.4, 128.6, 74.7, 49.2; $CH_2$: 34,6, 34.4, 33.9, 32.1, 28.9, 20.1; IR (thin film): 1738, 1692, 1683 cm$^{-1}$; HRMS-ESI(m/z) [M]$^+$ calculated for $C_{14}H_{16}O_2Na$=239.1048; found 239.1057.

The compound (±)-9-Methyl-1,2,3,6,6a,8,9,9a, 10,10a-decahydro-7H-3a,6-epoxydicyclopenta[a,d] [8]annulen-7-one (9) was made according to the following procedure. In a glove box, CuI (1.11 g, 5.75 mmol) was weighed into a 250 mL reaction flask. The flask was sealed and removed from the glove box. A suspension of CuI in THF (36 mL) was cooled to 0° C. and MeLi (7.2 mL, 1.6M, 12 mmol) was added drop wise over 15 min. The resulting slurry was stirred at 0° C. for 15 minutes, then cooled to −78° C. A separate flask was charged with compound 8a (0.622 g, 2.88 mmol) and TMSCl (1.8 mL, 14 mmol) in THF (20 mL). This solution was added drop-wise to the suspension of $Me_2CuLi$ at −78° C. over 1.5 hour via syringe pump. The reaction was maintained at −78° C. for 5 hours, then quickly poured into a slurry of $Et_3N$ (13.4 mL) and florisil (15 g) in hexanes (125 mL) at 0° C. After 1 hour, the slurry was filtered and the filter cake was washed with hexanes (2×100 mL). The resulting solution was concentrated to a small volume under reduced pressure and filtered again. The filter cake was washed with hexanes (100 mL) and organic extracts were concentrated under reduced pressure to afford the corresponding silyl enol ether colorless oil: $^1$H NMR (600 MHz, $CDCl_3$) δ 5.98 (dd, J=5.8, 2.0, 1H), 5.74 (dd, J=5.8, 0.8, 1H), 5.43 (s, 1H), 2.46-2.41 (m, 1H), 2.33-2.30 (m, 1H), 2.00 (dd, J=15.2, 8.5, 1H), 1.97-1.91 (m, 1H), 1.85-1.81 (m, 1H), 1.77-1.62 (m, 3H), 1.55-1.49 (m, 2H), 1.39 (dd, J=13.4, 3.5, 1H), 1.34 (d, J=11.9, 1H), 1.17 (s, 3H), 1.15-1.10 (m, 1H), 0.18 (s, 9H); $^{13}$C NMR (150 MHz, $CDCl_3$) δC: 144.2, 126.2, 97.2, 47.0; CH: 132.4, 128.4, 79.7, 46.4; $CH_2$: 41.5, 39.6, 33.9, 31.6, 27.3, 19.8; $CH_3$: 24.9, 0.6.

A solution of the unpurified residue prepared above in THF (9 mL) was treated with 1 M HCl (5.6 mL, 5.6 mmol). The reaction was maintained at 23° C. for 1 hour, then transferred to a separatory funnel with ethyl acetate (25 mL). The aqueous layer was washed with ethyl acetate (3×25 mL). The combined organic layers were washed with brine (100 mL), dried over $Na_2SO_4$, filtered, and then concentrated under reduced pressure to afford compound 9 (1.34 g, 5.70 mmol, >95%) as a colorless solid. No further purification was necessary: mp=88.9-91.3° C.; $^1$H NMR (600 MHz, $CDCl_3$) δ 6.20 (dd, J=6.0, 1.5, 1H), 5.82 (d, J=6.1, 1H), 5.13 (d, J=8.2, 1H), 2.70 (d, J=8.1, 1H), 2.39-2.33 (m, 1H), 2.23 (dd, J=10.5, 5.9, 2H), 1.91-1.85 (m, 2H), 1.77-1.71 (m, 4H), 1.65-1.60 (m, 2H), 1.38 (s, 3H), 1.28 (dd, J=13.9, 2.4, 1H), 1.10-1.02 (m, 1H); $^{13}$C NMR (150 MHz, $CDCl_3$) δ C: 220.3, 97.6, 44.8; CH: 132.0, 131.4, 82.2, 63.8, 46.4; $CH_2$: 38.7, 38.4, 37.4, 32.8, 27.0, 20.3; $CH_3$: 30.9; HRMS-ESI (m/z) [M]+ calculated for $C_{15}H_{21}O_2$=233.1542; found 233.1548.

The compound (±)-9-methyl-2,3,6,8,9,9a, 10,10a-octahydro-1H-3a,6-epoxydicyclopenta[a,d][8]annulen-7-yl trifluoromethanesulfonate (10) was prepared according to the following procedure. A solution of ketone 9 (0.443 g, 1.91 mmol) in THF (19 mL) was cooled to −78° C. KHMDS (2.9 mL, 1.0 M) was added drop wise over 15 minutes and the reaction was maintained at −78° C. After 1 hour, the reaction mixture was treated with a solution of $PhNTf_2$ (0.81 g, 2.29, mmol) in THF (12 mL) at −78° C. After 2 hours, the reaction was quenched with $Et_3N$ (8.7 mL). The resulting mixture was warmed to room temperature, concentrated to a small volume, and purified by flash chromatography ($SiO_2$, 99:1 hexanes/$Et_3N$) to afford compound 10 (0.562 g, 1.55 mmol, 81%) as a yellow oil: $^1$H NMR (600 MHz, $CDCl_3$) δ 5.99 (dd, J=5.9, 2.0, 1H), 5.88 (dd, J=5.9, 0.8, 1H), 5.49 (s, 1H), 2.79-2.73 (m, 1H), 2.41-2.36 (m, 1H), 1.97-1.93 (m, 1H), 1.89-1.85 (m, 1H), 1.81-1.77 (m, 1H), 1.73-1.66 (m, 4H), 1.47 (dd, J=13.7, 3.4 1H), 1.42-1.38 (m, 1H), 1.26 (s, 3H), 1.16-1.13 (m, 1H); $^{13}$C NMR (150 MHz, $CDCl_3$) δC: 140.1, 139.3, 118.4 (q, J=318), 98.1, 47.6; CH: 130.6, 130.5, 78.4, 46.1; $CH_2$: 40.7, 38.9, 33.6, 28.9, 27.1, 19.8; $CH_3$: 24.0. HRMS-ESI (m/z) [M]+ calculated for $C_{16}H_{19}F_3O_4SNa$=387.0854; found 387.0868.

The compound (±)-9-Methyl-7-(prop-1-en-2-yl)-2,3,6,8, 9,9a,10,10a-octahydro-1H-3a,6-epoxydicyclopenta[a,d][8] annulene (11) was made according to the following procedure. A Schlenk tube charged with compound 10 (0.470, 1.29 mmol) and $Pd(dppf)Cl_2$ (0.094 g, 0.13 mmol) was sealed and placed under inert atmosphere. A THF solution of isopropenylmagnesium bromide (5.2 mL, 0.5 M, 2.6 mmol) was added drop wise over 5 minutes to the Schlenk tube at room temperature. The resulting solution was warmed to 55° C. After 7 hours, the reaction was cooled to room temperature and quenched with saturated aqueous $NH_4Cl$ (5.5 mL). The resulting slurry was transferred to a separatory funnel and extracted with EtOAc (3×10 mL). The combined organic extracts were washed with brine (50 mL), dried over $MgSO_4$, filtered, and concentrated under reduced pressure. The resulting crude residue was purified by flash column ($SiO_2$, 99:1 hexane/$Et_2O$) to yield 11 (0.269 g, 1.07 mmol, 82%) as a colorless oil: $^1$H NMR (600 MHz, $CDCl_3$) δ5.93 (dd, J=5.9, 1.9, 1H), 5.80 (d, J=5.9, 1H), 5.60 (s, 1H), 4.91 (s, 1H), 4.70 (s, 1H), 2.59-2.53 (m, 1H), 2.39-2.33 (m, 1H), 2.17-2.13 (m, 1H), 1.97-1.92 (m, 1H), 1.83 (s, 3H) 1.78-1.67 (m, 4H), 1.54-1.51 (m, 2H), 1.47 (dd, J=13.6, 3.4 1H), 1.41-1.37 (m, 1H), 1.18 (s, 3H), 1.16-1.11 (m, 1H); $^{13}$C NMR (150 MHz, $CDCl_3$) SC: 146.0, 141.9, 134.8 97.6 51.9; CH: 132.5, 129.4, 81.6, 46.3; $CH_2$: 112.8, 40.9, 40.3, 33.6, 32.8, 27.1, 19.9; $CH_3$: 24.0, 22.8. IR (thin film): 1734, 1626 cm.$^{-1}$ Example 4—Further Synthetic Procedures A concise route to photosubstrate 4 was devised that was flexible and amenable to scale:

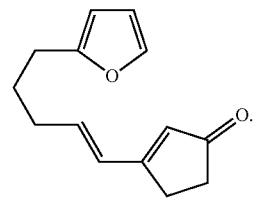

4

As shown in the following scheme, a large-scale protocol was established, as described herein, for the alkylation of 5-iodopentyne (7) with 2-furyllithium to give 8 in 91% yield. Subsequent exposure of 8 to Schwartz's reagent formed vinyl zirconium 9.

1.

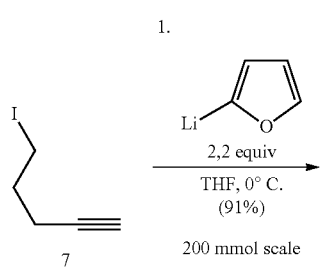

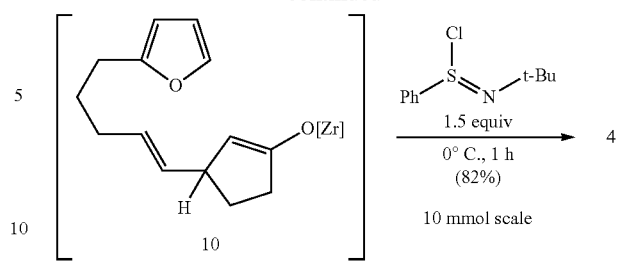

2. ZrCp₂HCl
THF, rt

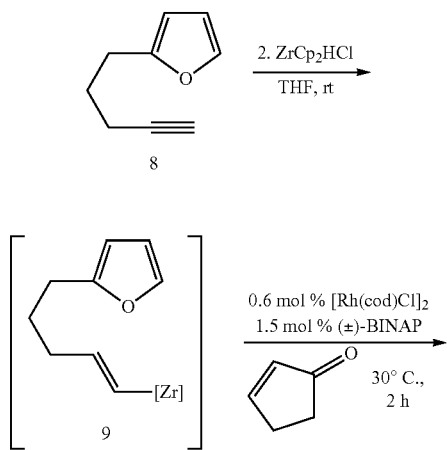

This species, i.e., vinyl zirconium 9, was then added to a solution of cyclopentenone and catalytic amounts of [Rh(cod)Cl]₂ and (±)-BINAP in THF. Warming the resulting solution to 30° C. for 2 hours formed zirconium enolate 10, which was cooled to 0° C., and exposed to N-tert-butylbenzenesulfinimidoyl chloride to afford 4 in 82% yield.

The two-operation sequence, at least in this example, allowed the preparation of gram quantities of 4 in a single pass. Moreover, the components within this scheme were varied to generate 10 derivatives of 4 for subsequent studies (see below).

In view of the synthesis of 4, the chemistry of the following scheme was implemented:

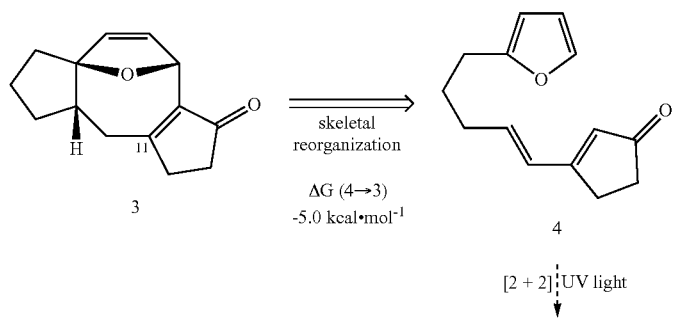

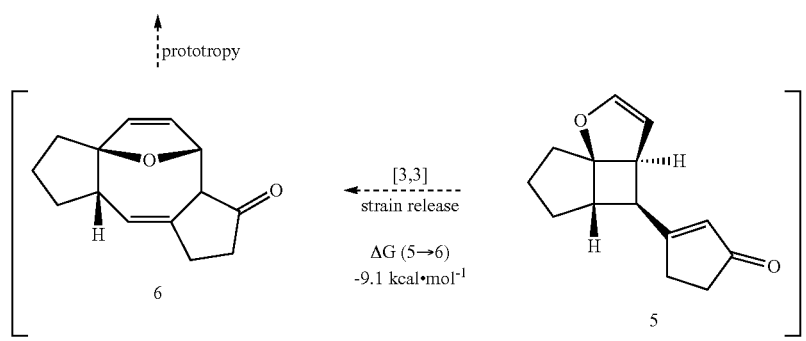

Solutions of 4 were exposed to UV-light (hv=350 nm) to generate cyclobutane 5. After testing, MeCN and n-BuOH were identified as preferred solvents for the [2+2] photocycloaddition. Irradiation of 4 in MeCN (60 mM, 35° C.) furnished 5 as a single diastereomer, as shown in the following scheme:

a. [2 + 2]-Photocycloaddition of 4

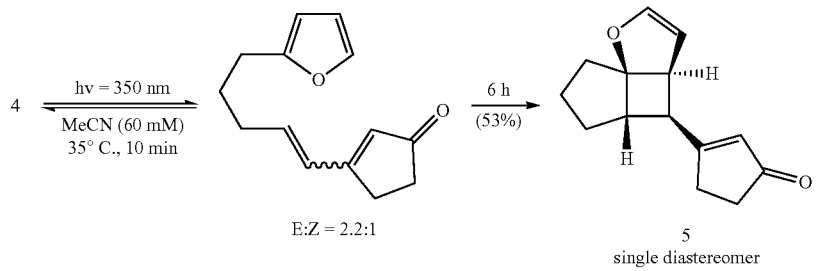

b. Photodecomposition of 5

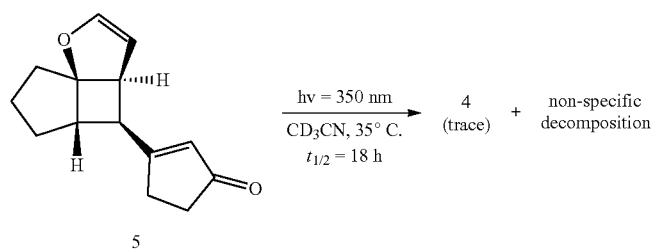

c. Thermal isomerization of 5 to 3

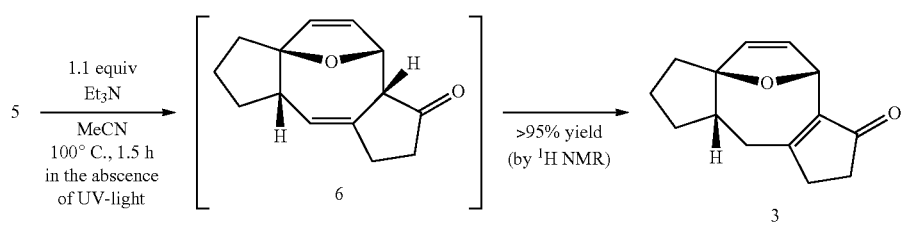

This reactive species was isolated as a crystalline solid in 53% yield. The remaining mass balance of the reaction was largely an isomeric mixture of E- and Z-4. Further analysis revealed that UV-light promoted isomerization of the acyclic alkene within 4. This reaction reached equilibrium within 10 minutes (E:Z ratio=2.2:1). Increasing the photoreaction time to 12 hours increased the extent of decomposition, which resulted in a relatively low yield of 5. The addition of triplet sensitizers (e.g., benzophenone) to the reaction media had no beneficial effect.

The stability of 5 was analyzed. Exposure of 5 to what were believed to be favorable photochemical conditions (hv=350 nm, 60 mM CD$_3$CN, 35° C.) resulted in slow decomposition and trace cycloreversion to 4 over 24 hours. Alternatively, when 5 was protected from light and heated above 35° C., gradual formation of cyclooctene isomers 6 and 3 were observed.

After further experimentation, it was found that 5 rearranged to 6 when heated to 100° C. for 1.5 hours. Subsequent isomerization of 6 to enone 3 occurred slowly under neutral conditions, allowing for the crystallization of 6 from toluene.

In contrast, exposure of 6 to Et$_3$N or silica gel promoted the rapid formation of 3. It was found that 5 rearranged to 3 in quantitative yield when heated to 100° C. in the presence of Et$_3$N.

The experiments of this example established a stereocontrolled mechanism for the cycloisomerization of 4 to fused 5-8-5 carbotricycle 3 by way of cyclobutane 5.

A procedure to convert 4 to ring system 3 in a single operation was developed. Results from the studies of this example are summarized at the following table:

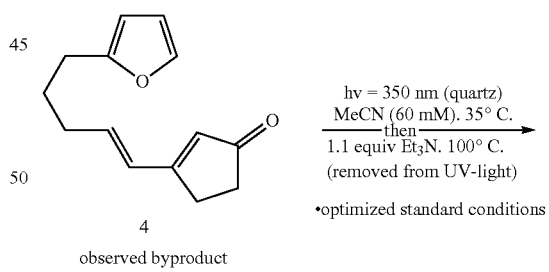

observed byproduct

*optimized standard conditions

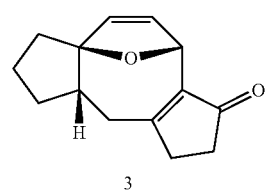

3

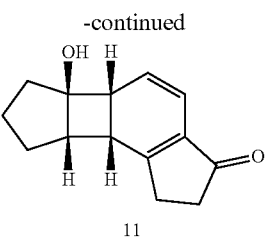

11

| entry | modification[a,b,c] | time (h)[d] | 3 (%)[e] | recovered 4 (%) |
|---|---|---|---|---|
| 1 | none | 12/6 | 51 | 26 |
| 2 | n-BuOH | 12/2 | 67 | 9 |
| 3 | n-BuOH, no Et₃N | 12/2 | 50[f] | 14 |
| 4 | hv at 65° C. | 21/0 | 18 | 0 |
| 5 | hv at 6° C., n-BuOH | 8/0 | 36 | 0 |
| 6 | hv at 65° C. with Et₃N | 24/0 | 24 | 0 |
| 7 | none, gram-scale | 55/6 | 61 | 24 |
| 8 | H-BuOH. grain-scale | 34/2 | 59 | 22 |

Reactions carried out on 0.5 mmol scale (108 mg of 4) were compared. The best results of this example were achieved using a two-stage protocol, wherein a solution of 4 in MeCN (60 mM) was reacted at 35° C. in a Rayonet. After 12 hours, the reaction mixture was moved to the bench-top, treated with Et₃N (1.1 equivalents), and warmed to 100° C. for 6 hours. This procedure afforded 3 in 51% yield along with 26% of unreacted 4 (entry 1 of the foregoing table).

Figure 4:
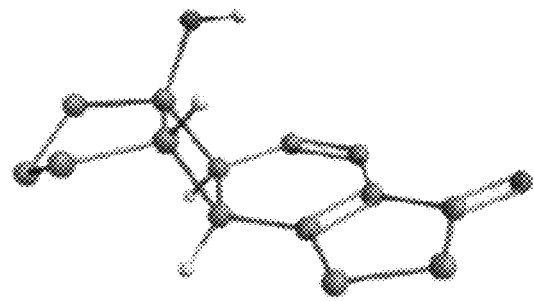
FIG. 4 depicts a three-dimensional X-ray structure of a compound described herein.

It was found that n-BuOH was a practical alternative for MeCN, providing 3 in 67% yield (entry 2 of the foregoing table). Importantly, addition of Et₃N to the reaction was required to suppress formation of by-product 11 (entry 3 of the foregoing table). FIG. 4 depicts a three-dimensional X-ray structure of by-product 11.

Also explored were conditions to execute the [2+2] cycloaddition and Cope rearrangement in tandem at 65° C. when exposed to UV-light. Alternatively, it was found that the two-stage procedure of this example could be scaled without loss of reaction efficiency (entries 7-8 of the foregoing table). Increased reaction times were required for photoreactions carried out on scale (55 hours in MeCN); however, gram quantities of 4 were processed to 3 in 61% yield (85% yield based on recovered 4) employing these otherwise exceedingly mild conditions.

The scope of the example of this process also was explored. Utilizing a two-step assembly described in the foregoing scheme of this example, a library of 10 representative tethers 12 was prepared that would produce variable substitution patterns around the 5-8-5 core of 2, as shown here:

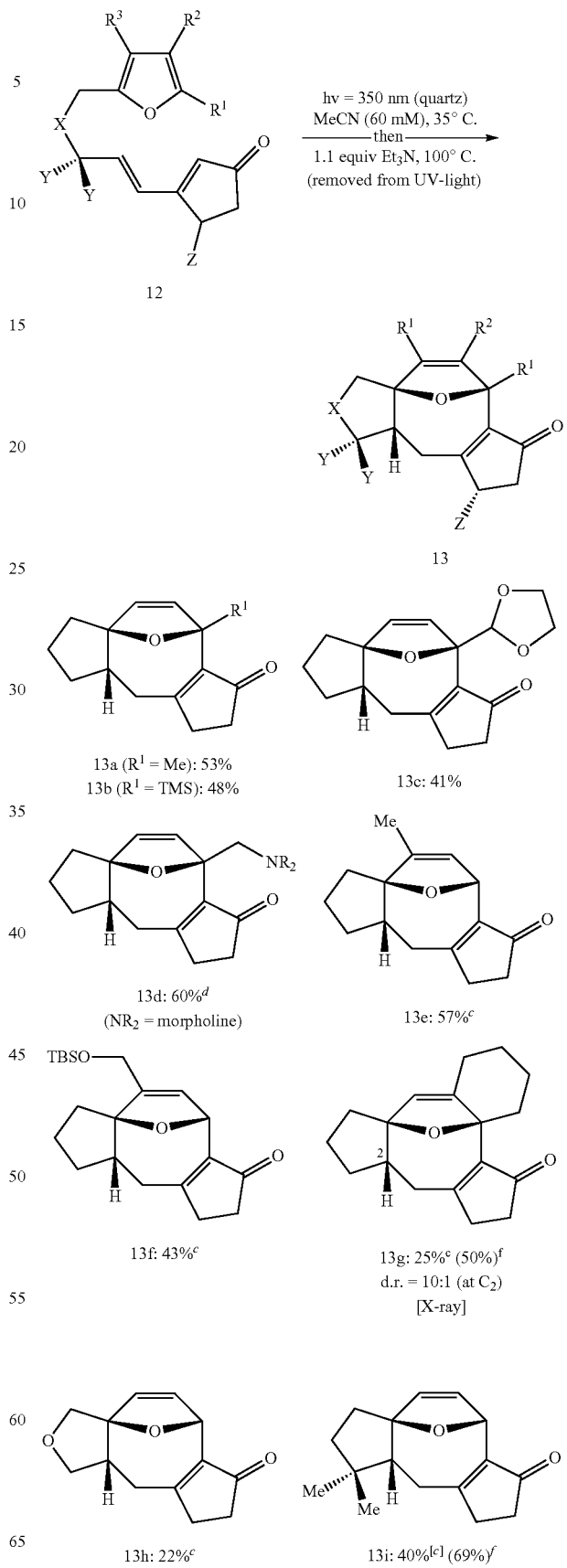

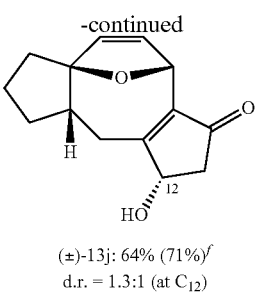

(±)-13j: 64% (71%)^f
d.r. = 1.3:1 (at C₁₂)

Tethers with modifications to the furan subunit (R¹-R³) reacted to give B-ring variants 13a-f in 41-60% yield. In each case, formation of a single diastereomer was observed. The lone exception was 12 g, which afforded 13 g in 25% yield along with small amounts of the corresponding $C_2$ diastereomer. (d.r.=10.1).

Similarly, substrates harboring changes to the hydrocarbon linker (i.e., X and Y) gave A-ring analogs 13h and 13i as single diastereomers in 22% and 40% yield, respectively. These compounds were markedly more challenging to isolate from impurities. Also examined was the isomerization of chiral tether (±)-12j (Z=OH), which afforded C-ring derivative (±)-13j as a mixture of diastereomers (d.r.=1.3:1 at C12) in 64% combined yield.

With a rapid and general entry to the 5-8-5 ring system in place, conditions were identified in this example to install the quaternary methyl group at C11. Exposure of enone 3 to lithium dimethylcuprate and TMSCl at −78° C. generated silyl enol ether 14 as a single diastereomer. This reaction was carried out on gram-scale, without the need for chromatography, to afford 14 in >95% yield. Subsequent hydrolysis of 14 with 1 M aq. HCl gave ketone 15 as a crystalline solid, allowing the relative stereochemistry of 1,4-addition by single-crystal X-ray diffraction to be established.

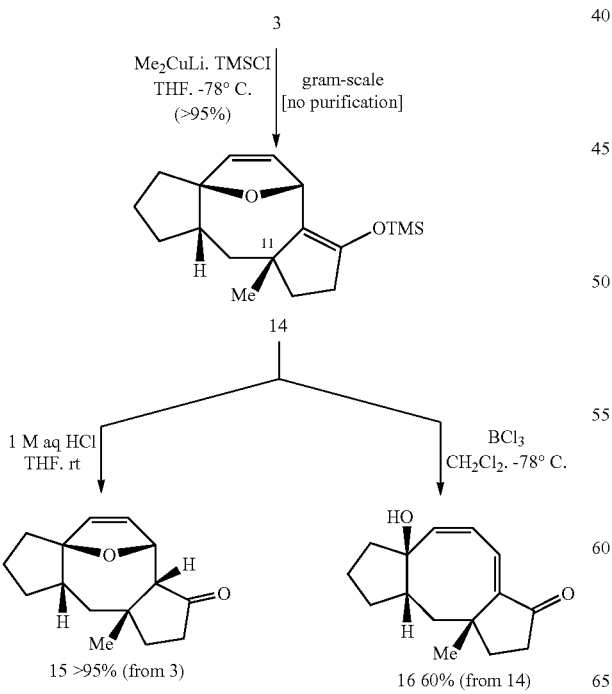

Figure 5:
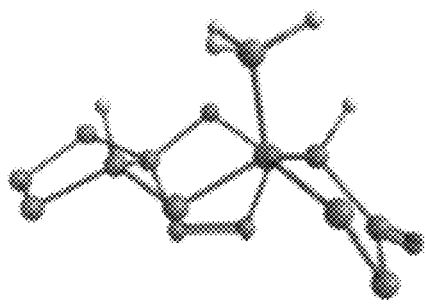
FIG. 5 depicts a three-dimensional X-ray structure of a ketone described herein.
Figure 6:
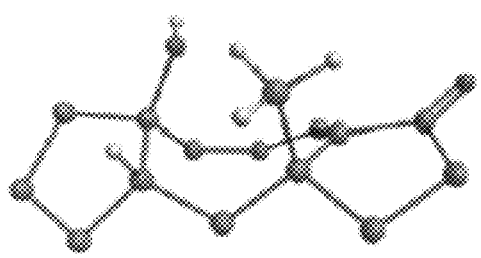
FIG. 6 depicts a three-dimensional X-ray structure of a dienone described herein.

Alternatively, it was found that addition of $BCl_3$ to a cooled solution of 14 resulted in ring-opening of the oxabicycle to afford conjugated dienone 16. Notably, the chemistry of this example established a scalable entry point to variations of 2 in four steps from widely available starting materials. FIG. 5 and FIG. 6 depict a three-dimensional X-ray structure of ketone 15 and dienone 16, respectively.

We claim:

1. A method of forming a fusicoccane derivative formula (B)

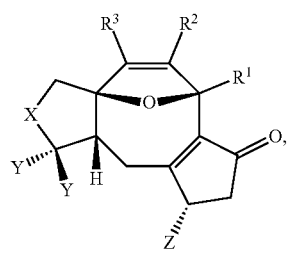

Formula (B)

the method comprising:
providing a tethered chromophore having a structure according to Formula (A)—

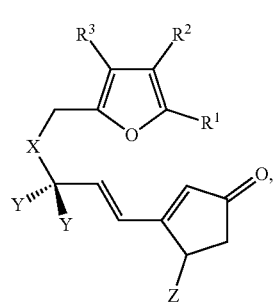

Formula (A)

wherein R¹, R², R³, Y, and Z are independently selected from the group consisting of hydrogen, a monovalent $C_1$-$C_{20}$ hydrocarbyl, hydroxyl, and a protecting group, and X is —$CH_2$— or oxygen; and
contacting the tethered chromophore with light comprising one or more wavelengths effective to initiate a photoinduced pericyclic reaction cascade to form a 5-8-5 carbotricycle.

2. The method of claim 1, wherein the providing of the tethered chromophore comprises:
contacting a 5-halopent-1-yne with a furyl-metal reagent to form an alkyl furan; and
contacting the alkyl furan with a cyclopentenone derivative to form the tethered chromophore.

3. The method of claim 2, wherein the 5-halopent-1-yne has a structure according to the following formula:

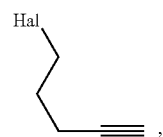

wherein Hal is Cl, Br, or I.

4. The method of claim 2, wherein the furyl-metal reagent comprises a compound having a structure according to the following formula:

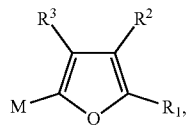

wherein $R^1$, $R^2$, and $R^3$ are independently selected from the group consisting of hydrogen, the monovalent $C_1$-$C_{20}$ hydrocarbyl, and the protecting group, and M is an alkali metal.

5. The method of claim 4, wherein M is lithium.

6. The method of claim 1, wherein $R^1$, $R^2$, and $R^3$ are hydrogen.

7. The method of claim 1, wherein two of $R^1$, $R^2$, and $R^3$ are hydrogen, and one of $R^1$, $R^2$, and $R^3$ is the monovalent $C_1$-$C_{20}$ hydrocarbyl or the protecting group.

8. The method of claim 1, wherein $R_1$ and $R_2$ are hydrogen, and $R_3$ is a methyl.

9. The method of claim 1, wherein $R_1$ and $R_2$ are hydrogen, and $R_3$ is the protecting group.

10. The method of claim 1, wherein $R_2$ and $R_3$ are hydrogen, and $R_1$ is [1] 1,3-dioxolan-2-yl, [2] a $C_1$-aldehyde, or [3] morpholin-4-yl.

11. The method of claim 1, wherein $R_3$ is a methyl or a $C_1$-alcohol, and $R_1$ and $R_2$ are hydrogen.

12. The method of claim 2, wherein the cyclopentenone derivative has a structure according to the following formula:

wherein Z is selected from the group consisting of hydrogen, the monovalent $C_1$-$C_{20}$ hydrocarbyl, the hydroxyl, and the protecting group.

13. The method of claim 12, wherein Z is hydrogen.

14. The method of claim 12, wherein Z is the hydroxyl.

15. The method of claim 12, wherein Z is the protecting group.

16. The method of claim 1, further comprising:
contacting the 5-8-5 carbotricycle with $(C_1$-$C_{20}$ hydrocarbyl)$_2$CuLi to form a conjugate alkylation product;
contacting the alkylation product with a deprotonating agent and a leaving group precursor to form an enol product; and
contacting the enol product with $(C_1$-$C_{20}$ hydrocarbyl)Mg(halogen) to form a functionally active derivative, wherein the halogen is selected from Cl, Br, or I.

17. The method of claim 16, wherein the $(C_1$-$C_{20}$ hydrocarbyl)$_2$CuLi is Me$_2$CuLi.

18. The method of claim 16, wherein the halogen is Br, and the $(C_1$-$C_{20}$ hydrocarbyl)Mg(halogen) is isopropenyl magnesium bromide.

19. A compound having a structure according to Formula (B):

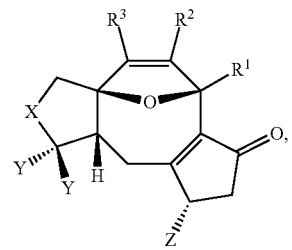

Formula (B)

wherein $R^1$, $R^2$, $R^3$, Y, and Z are independently selected from the group consisting of hydrogen, a monovalent $C_1$-$C_{20}$ hydrocarbyl, hydroxyl, and a protecting group; and X is —CH$_2$— or oxygen.

20. The compound of claim 19, wherein the compound has a structure according to one of Formulas B1-B9:

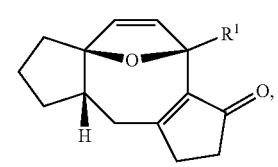

(Formula B1)

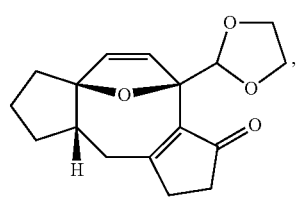

(Formula B2)

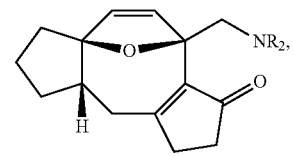

(Formula B3)

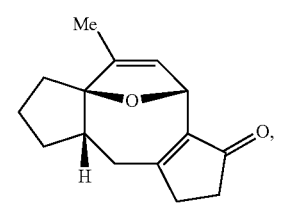

(Formula B4)

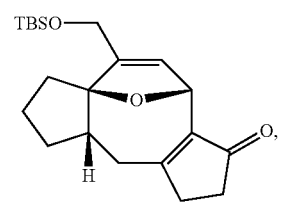

(Formula B5)

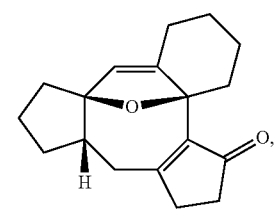

(Formula B6)

(Formula B7)
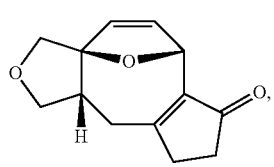
(Formula B8)
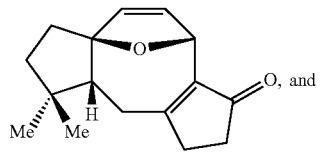
O, and
(Formula B9)
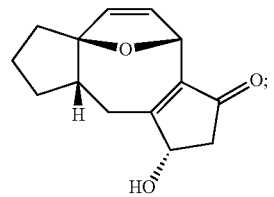
wherein $R^1$ is methyl or trimethylsilyl.
* * * * *